United States Patent
Nozato et al.

(10) Patent No.: US 8,646,911 B2
(45) Date of Patent: Feb. 11, 2014

(54) COMPENSATION OPTICAL APPARATUS AND IMAGE SENSING APPARATUS

(75) Inventors: Koji Nozato, Yokohama (JP); Takeshi Kitamura, Port Washington, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 8 days.

(21) Appl. No.: 13/575,584

(22) PCT Filed: Jan. 14, 2011

(86) PCT No.: PCT/JP2011/051038
§ 371 (c)(1),
(2), (4) Date: Jul. 26, 2012

(87) PCT Pub. No.: WO2011/093208
PCT Pub. Date: Aug. 4, 2011

(65) Prior Publication Data
US 2012/0293771 A1     Nov. 22, 2012

(30) Foreign Application Priority Data
Jan. 29, 2010  (JP) ................................. 2010-019120

(51) Int. Cl.
    *A61B 3/10*        (2006.01)
    *A61B 3/107*      (2006.01)

(52) U.S. Cl.
    CPC ............... *A61B 3/1015* (2013.01); *A61B 3/107* (2013.01)
    USPC ............................ 351/205; 351/210; 356/512

(58) Field of Classification Search
    CPC ............................... A61B 3/1015; A61B 3/107
    USPC ................... 351/205, 210, 246; 356/511, 512
    See application file for complete search history.

(56) References Cited

U.S. PATENT DOCUMENTS

| 6,186,628 | B1 | 2/2001 | Van de Velde |
| 7,281,797 | B2 * | 10/2007 | Yamaguchi et al. ........... 351/205 |
| 2007/0252951 | A1 | 11/2007 | Hammer et al. |
| 2010/0321675 | A1 * | 12/2010 | Huang et al. ................... 356/217 |

FOREIGN PATENT DOCUMENTS

| JP | 2006-330040 A | 12/2006 |
| WO | 03/020121 A | 3/2003 |

OTHER PUBLICATIONS

International Preliminary Report on Patentability (IPRP) issued Aug. 9, 2012 in related International Application No. PCT/JP2011/051038.

(Continued)

*Primary Examiner* — Huy K Mai
(74) *Attorney, Agent, or Firm* — Canon USA Inc IP Division

(57) ABSTRACT

A compensation optical apparatus for obtaining and image of an object without reduction in image quality irrespective of aberration compensation, includes: a division unit for dividing a return beam from a measured object; an aberration measurement unit for measuring an aberration caused by the measured object, with a divided beam from the division unit; an aberration compensation unit for performing aberration compensation based on the aberration measured by the aberration measurement unit; a projection unit for projecting a beam obtained by the aberration compensation in the aberration compensation unit to the measured object; an acquirement unit for acquiring a value exhibiting a state of the measured object based on the return beam from the measured object, which is obtained by the beam projected from the projection unit; and a control unit for retreating the division unit from an optical path based on the value acquired by the acquirement unit.

15 Claims, 8 Drawing Sheets

(56) References Cited

OTHER PUBLICATIONS

Y. Zhang et al., "Adaptive Optics Parallel Spectral Domain Optical Coherence Tomography for Imaging the Living Retina" Optics Express, (Optical Society of America), Washington DC (US) vol. 13, No. 12, Jun. 2005, pp. 4792-4811.

Yan Zhang et al., High-Speed Volumetric Imaging of Cone Photoreceptors with Adaptive Optics Spectral-Domain Optical Coherence Tomography, Optics Express, 14, 10:4380-4394, May 15, 2006, Optical Society of America, Washington, D.C.

* cited by examiner

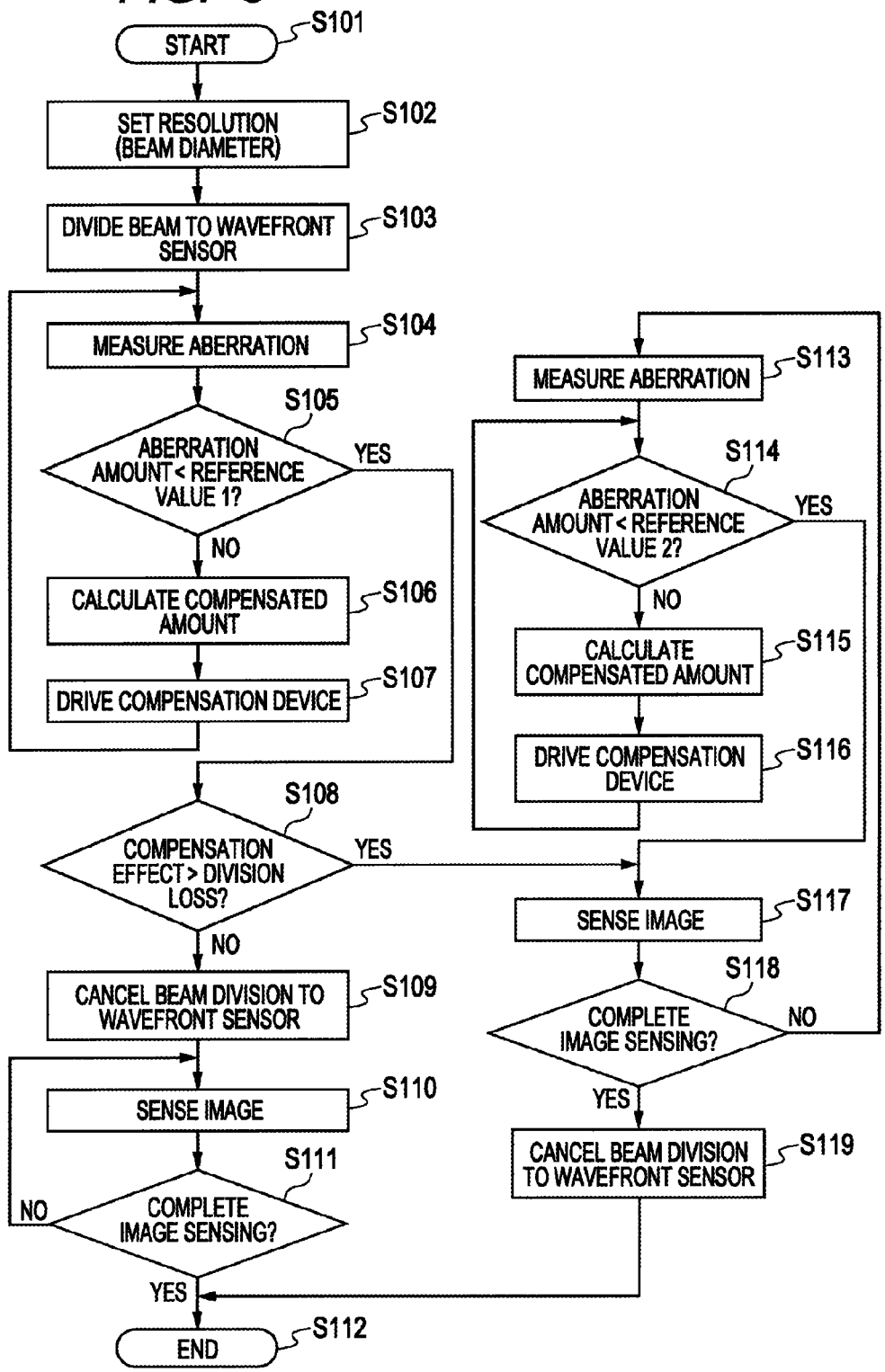

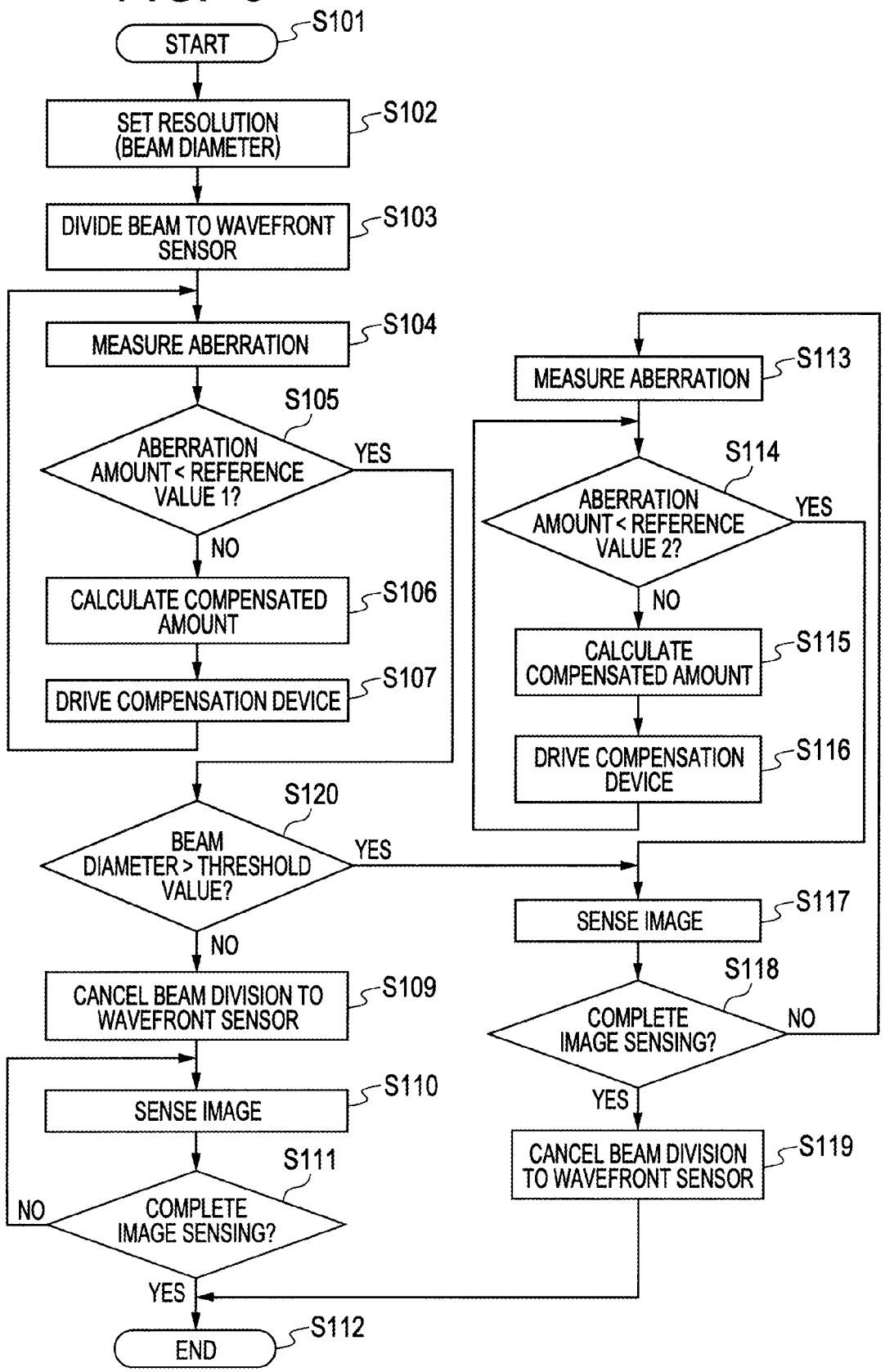

COMPENSATION OPTICAL APPARATUS AND IMAGE SENSING APPARATUS

TECHNICAL FIELD

The present invention relates to a compensation optical apparatus and an image sensing apparatus including the compensation optical apparatus, for sensing an image of a measured object.

BACKGROUND ART

Major examples of an ophthalmologic image sensing apparatus are a scanning laser ophthalmoscope (SLO) and an optical coherence tomography (OCT) apparatus. Major examples of the OCT are a Time Domain OCT (TD-OCT) and a Spectral Domain OCT (SD-OCT).

In order to improve the resolution of a fundus image of an eye to be inspected, an attempt has been made to increase NA of a light projection system for the eye to be inspected. Measuring light projected to the fundus passes through optical tissues of the eye to be inspected, such as a cornea and a crystalline lens, and is affected by aberrations of the optical tissues. When the aberrations are large, there is a case where the quality of the fundus image is not improved by the increase in NA.

In view of the above, NPL 1 discloses an adaptive optics OCT (AO-OCT) which incorporates into the OCT an adaptive optics (AO) system in which aberration measurement and aberration compensation are repeated at high speed to precompensate for an aberration of the measuring light, which is caused in the irradiated eye to be inspected, based on a measured aberration.

In the AO-OCT, aberration of light obtained by dividing a return beam from the eye to be inspected is measured. Therefore, an intensity of the return beam to be used for the fundus image reduces, and hence the quality of the fundus image degrades. Even when the intensity of light entering the eye to be inspected is increased in advance to compensate for the reduction in intensity of the return beam which is caused by the division, there is a limit because the intensity of the incident light is limited in under safety standards. Thus, it is necessary to minimize the intensity of the light obtained by dividing the return beam for aberration measurement. On the other hand, in order to perform aberration compensation in short time, short-time aberration measurement is required. Therefore, it is necessary to maximize the intensity of light for aberration compensation.

CITATION LIST

Non Patent Literature

NPL 1: Y. Zhang et al, Optics Express, Vol. 14, No. 10, May, 2006

SUMMARY OF INVENTION

Technical Problem

The degree of improvement on image quality due to aberration compensation varies depending on a value exhibiting a state of a measured object (also referred to as image sensing condition, for example, aberration amount of anterior portion of eye to be inspected or aberration change amount thereof). When the intensity of the return beam reduces because of the division, the image quality after aberration compensation may be reduced to less than the image quality before aberration compensation, depending on the value.

Solution to Problem

A compensation optical apparatus according to the present invention includes; a division unit for dividing a return beam from a measured object, an aberration measurement unit for measuring an aberration caused by the measured object, with a divided beam from the division unit, an aberration compensation unit for performing aberration compensation based on the aberration measured by the aberration measurement unit, a projection unit for projecting a beam obtained by the aberration compensation in the aberration compensation unit to the measured object, an acquirement unit for acquiring a value exhibiting a state of the measured object based on the return beam from the measured object, which is obtained by the beam projected from the projection unit, and a control unit for retreating the division unit from an optical path based on the value acquired by the acquirement unit.

Advantageous Effects of Invention

According to the compensation optical apparatus of the present invention, the unit for dividing a part of return beam based on the value exhibiting the state of the measured object (for example, aberration amount of anterior portion of eye to be inspected) to guide the part of the return beam to the aberration measurement unit may be retreated. Therefore, even when image quality after aberration compensation becomes lower than image quality before aberration compensation, because an intensity of the return beam is not reduced by the division, an image of the measured object may be obtained without the reduction in image quality.

Further features of the present invention will become apparent from the following description of exemplary embodiments with reference to the attached drawings.

BRIEF DESCRIPTION OF DRAWINGS

FIGS. 2A, 2B, 2C-1, 2C-2, 2D, 2E-1, and 2E-2 are schematic views illustrating a wavefront compensation device and a wavefront sensor in the first embodiment of the present invention, in which FIG. 2A is a schematic view illustrating a reflection type liquid crystal optical modulator, FIG. 2B is a schematic diagram illustrating a variable shape mirror, FIGS. 2C-1 and 2C-2 are schematic views illustrating a structure of a Shack-Hartmann sensor, FIG. 2D is a schematic view illustrating a state in which a light beam for wavefront measurement is focused on a CCD sensor, and FIGS. 2E-1 and 2E-2 are schematic views illustrating a case where a wavefront having a spherical aberration is measured.

FIG. 3 is a flow chart illustrating a procedure of the control method for the optical image sensing apparatus according to the first embodiment of the present invention.

FIG. 5 is a flow chart illustrating a procedure of a control method for an optical image sensing apparatus according to a second embodiment of the present invention.

DESCRIPTION OF EMBODIMENTS

According to a compensation optical apparatus of the present invention, a unit for dividing a part of return beam based on a value exhibiting a state of a measured object (for example, value exhibiting the quality of an image including at least one of a resolution and an intensity, aberration amount of anterior portion of eye to be inspected, and change amount of aberration) to guide the part of the return beam to an aberration measurement unit (division unit) may be retreated. Therefore, even when image quality after aberration compensation becomes lower than image quality before aberration compensation, because an intensity of the return beam is not reduced by the division, an image of the measured object may be obtained without the reduction in image quality.

The present invention is described with reference to the following embodiments.

The present invention is not limited by the following structures according to the respective embodiments.

First Embodiment

A first embodiment describes a structural example in which the present invention is applied to a scanning laser ophthalmoscope (SLO) provided with a compensation optical function.

Figure 1:
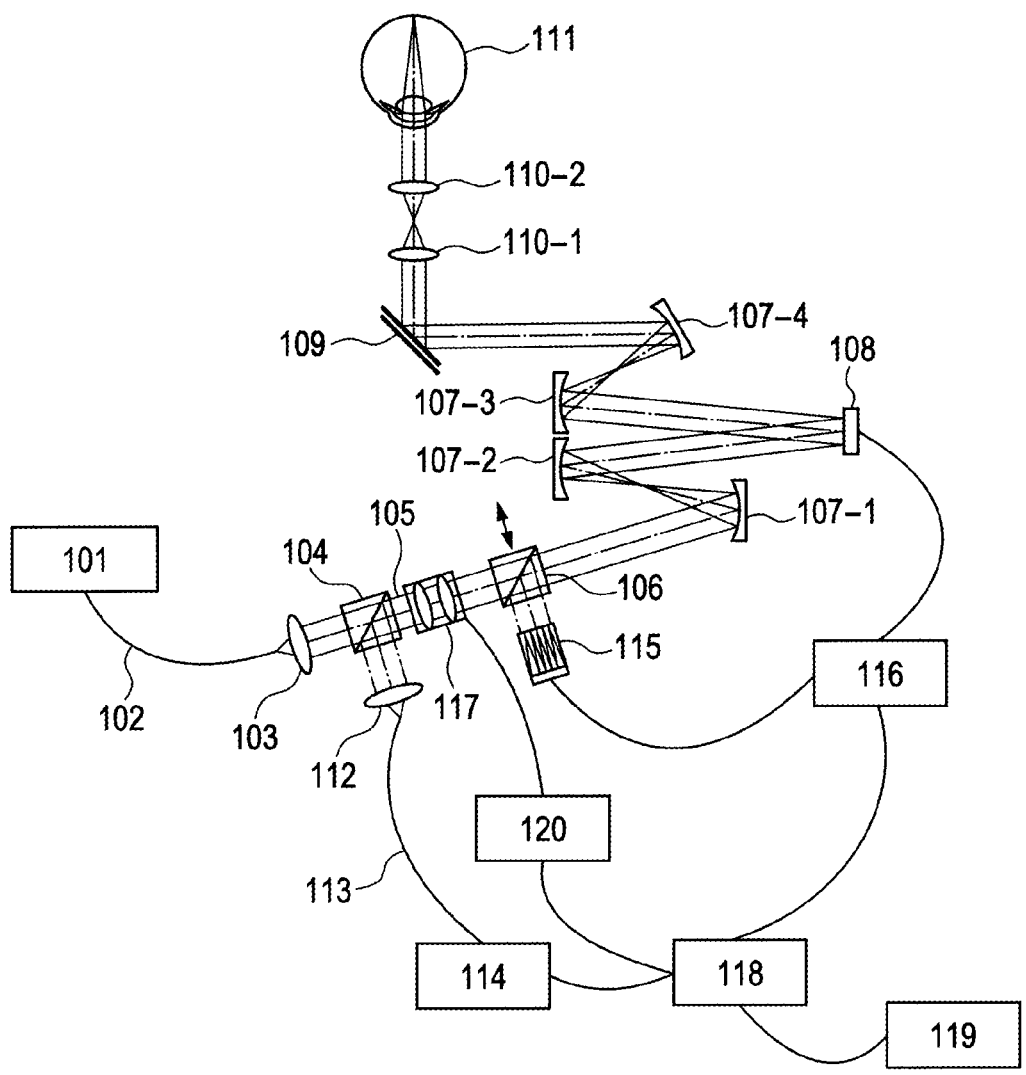
FIG. 1 is a schematic diagram illustrating a structural example of a scanning laser ophthalmoscope (SLO) used for a control method for an optical image sensing apparatus according to a first embodiment of the present invention.

FIG. 1 is a schematic diagram illustrating a structural example of the SLO.

In FIG. 1, a light source 101 used in this embodiment is a super luminescent diode (SLD) light source having a wavelength of 840 nm.

The wavelength of the light source 101 is not particularly limited. The wavelength of the light source 101 for fundus image sensing is suitably set in a range of approximately 800 nm to 1,500 nm in order to reduce glare for a person to be inspected and maintain a resolution.

In this embodiment, the SLD light source is used. In addition to such light source, for example, a laser light source may be used.

In this embodiment, the light source is used in common for fundus image sensing and wavefront measurement. A structure may be employed in which respective light sources are provided separately and light beams therefrom are superimposed on each other on an optical path.

As illustrated in FIG. 1, light projected from the light source 101 passes through a single-mode optical fiber 102, and is converted into collimated light by a collimator 103 are projected.

Measuring light 105 projected from the collimator 103 passes through a light division portion 104 including a beam splitter and then enters a resolution setting unit 117.

The resolution setting unit 117 (also referred to as varying unit for varying beam diameter or reducing beam diameter) varies the beam diameter of the incident measuring light 105 to project the incident measuring light 105, to thereby change an image sensing resolution.

When the beam diameter is varied in a range of approximately 7 mm to 1 mm, the image sensing resolution on the fundus may be set in a range of approximately 3 μm to 20 μm.

It is useful to make the image sensing resolution variable, in order to lower the image sensing resolution to reduce a data amount when an image is to be sensed at a wide viewing angle, in order to adjust the image sensing resolution based on the aberration of the eye to be inspected, or in order to sense an image using a narrow beam passing around a low-transmittance portion depending on an image sensing method.

The resolution setting unit 117 is controlled by a resolution controller 120. The resolution controller 120 operates in conjunction with a control unit 118.

The resolution setting unit 117 suitably has a structure including multiple lenses to adjust a positional relationship therebetween, and may have a structure for continuously changing a resolution or a structure for discretely changing a resolution.

The measuring light 105 passing through the resolution setting unit 117 is guided to a compensation optical system.

The compensation optical system includes a light division portion (corresponding to division unit in this embodiment) 106, a wavefront sensor (corresponding to aberration measurement unit in this embodiment) 115, a wavefront compensation device (corresponding to aberration compensation unit in this embodiment) 108, and reflective mirrors 107-1 to 107-4 for guiding the measuring light 105 to those components. The light division portion 106 and the wavefront sensor 115 are provided on a stage (not shown) to be inserted into an optical path of the measuring light 105 as described later.

The reflective mirrors 107-1 to 107-4 are provided so that at least a pupil of the eye, the wavefront sensor 115, and the wavefront compensation device 108 are in an optically conjugate relationship. In this embodiment, a beam splitter is used as the light division portion 106.

The measuring light 105 passing through the light division portion 106 enters the wavefront compensation device 108.

The measuring light 105 reflected on the wavefront compensation device 108 travels to the reflective mirror 107-3.

In this embodiment, a spatial phase modulator including a liquid crystal element is used as the wavefront compensation device 108.

Figure 2A:
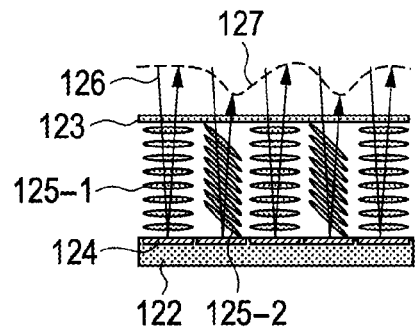

FIG. 2A is a schematic view illustrating a reflection type liquid crystal optical modulator used as an example of the spatial phase modulator in this embodiment.

The reflection type liquid crystal optical modulator has a structure in which liquid crystal molecules 125 are filled into a space surrounded by a base portion 122 and a cover 123.

The base portion 122 includes multiple pixel electrodes 124. The cover 123 includes a transparent counter electrode (not shown).

When no voltages are applied between the pixel electrodes and the counter electrode, the liquid crystal molecules are in such an orientation state as the liquid crystal molecules 125-1. When voltages are applied, the orientation state is changed to such an orientation state as the liquid crystal molecules 125-2, and hence a refractive index with respect to incident light changes.

When a voltage is controlled for each of the pixel electrodes to change a refractive index of each pixel, spatial phase modulation may be realized.

For example, when incident light 126 enters the liquid crystal element, light passing through the liquid crystal molecules 125-2 is delayed in phase from light passing through the liquid crystal molecules 125-1, to thereby form a wavefront 127 as illustrated in FIG. 2A.

The reflection type liquid crystal optical modulator generally includes several ten thousand to several hundred thousand pixels. The liquid crystal element has a polarization characteristic, and hence the reflection type liquid crystal optical modulator may include a polarization element for adjusting a polarization state of incident light.

Another example of the wavefront compensation device 108 is a variable shape mirror.

The variable shape mirror may locally change a light reflection direction, and various types of variable shape mirrors are put into practical use.

Figure 2B:
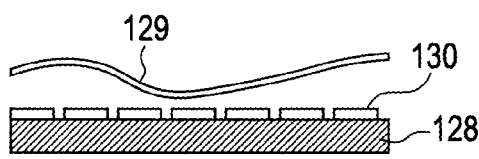

For example, there is a device as illustrated in a cross section view of FIG. 2B.

The device includes: a film-shaped mirror surface 129 which reflects incident light and is deformable; a base portion 128; actuators 130 interposed between the mirror surface 129 and the base portion 128; and a support portion (not shown) for supporting the periphery of the mirror surface 129.

The operational principles of the actuators 130 may be based on an electrostatic force, a magnetic force, or a piezoelectric effect. A structure of the actuators 130 varies depending on the operational principles.

The multiple actuators 130 are two-dimensionally arranged on the base portion 128 and selectively driven to be able to freely deform the mirror surface 129. The variable shape mirror generally includes several ten to several hundred actuators.

The light reflected on the reflective mirrors 107-3 and 107-4 is one-dimensionally or two-dimensionally scanned by a scanning optical system 109.

In this embodiment, two galvano-scanners are used as the scanning optical system 109 for main scanning (lateral direction of fundus) and sub scanning (longitudinal direction of fundus).

In order to sense an image at a higher speed, a resonance scanner may be used for the main scanning side of the scanning optical system 109.

In order to bring the respective scanners included in the scanning optical system 109 into an optically conjugate relationship, optical elements such as a mirror and a lens may be used between the respective scanners depending on a structure.

The measuring light 105 scanned by the scanning optical system 109 is projected to an eye 111 through eyepieces 110-1 and 110-2 serving as an eyepiece portion.

The measuring light projected to the eye 111 is reflected or scattered on the fundus to become a return beam. When the eyepieces 110-1 and 110-2 are adjusted in position, suitable projection may be performed according to the diopter of the eye 111.

The lenses are used for the eyepiece portion in this embodiment, but, for example, spherical mirrors may be used.

Reflected scattering light of the return beam which is produced by reflection or scattering on a retina of the eye 111 travels in the reverse direction on the same optical path as in the case of incidence. A part of the reflected scattering light is reflected by the light division portion 106 to the wavefront sensor 115 to be used for measuring a light beam wavefront.

In this embodiment, a Shack-Hartmann sensor is used as the wavefront sensor 115. The Shack-Hartmann sensor receives the reflected light resulting from the measuring light entering the eye by a CCD camera through a micro-lens array, to measure a wavefront.

The wavefront compensation device, for example, the variable shape mirror or the spatial phase modulator is driven so as to compensate for the measured wavefront to sense an image of the fundus through the device, and hence high-resolution image sensing may be achieved.

Figures 1, 2C:
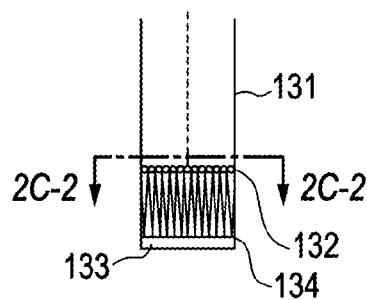

FIG. 2C-1 is a schematic view illustrating the Shack-Hartmann sensor.

A light beam 131 for wavefront measurement is focused on a focal surface 134 of a CCD sensor 133 through a micro-lens array 132.

Figures 2, 2C:
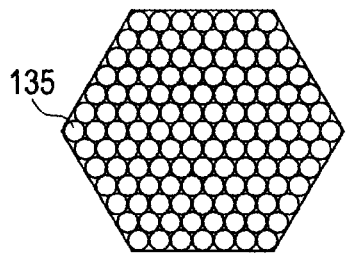

FIG. 2C-2 illustrates a state as viewed from a position indicated by 2C-2-2C-2 of FIG. 2C-1. The micro-lens array 132 includes multiple micro-lenses 135. The light beam 131 is focused on the CCD sensor 133 through the respective micro-lenses 135, and hence the light beam 131 is divided into spots equal in number to the micro-lenses 135 to form the spots.

Figure 2D:
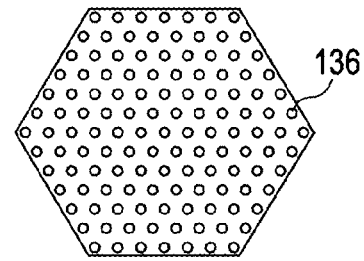

FIG. 2D illustrates a state in which the spots are formed on the CCD sensor 133. The light beam passing through the respective micro-lenses 135 is focused to form spots 136. A wavefront of the incident light beam is calculated based on the positions of the respective spots 136.

Figures 1, 2E:
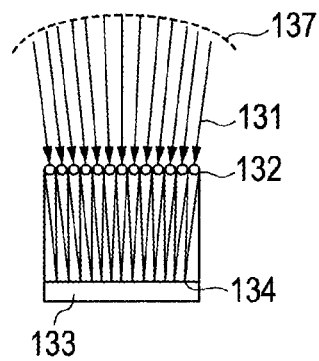
Figures 2, 2E:
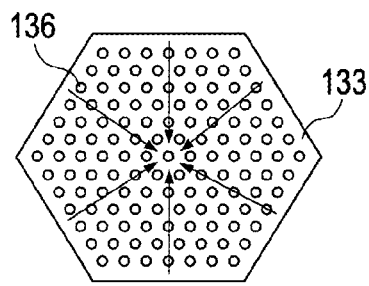

For example, FIG. 2E-1 is a schematic view illustrating a case where a wavefront having a spherical aberration is measured.

The light beam 131 is formed to have a wavefront 137.

The light beam 131 is focused at positions in a direction of the local normal to the wavefront by the micro-lens array 132.

A focal state on the CCD sensor 133 in this case is illustrated in FIG. 2E-2.

The light beam 131 has a spherical aberration, and hence the formed spots 136 are biased to the central portion. When the positions of the formed spots 136 are calculated, the wavefront of the light beam 131 may be determined. In this embodiment, the Shack-Hartmann sensor is used as the wavefront sensor. However, the present invention is not limited to this sensor. Another wavefront measurement unit, for example, a curvature sensor may be employed or a method of obtaining the wavefront by reverse calculation from the formed spot images may be employed.

When the reflected scattering light passes through the light division portion 106, a part thereof is reflected on the light division portion 104 and is guided to a light intensity sensor 114 through a collimator 112 and an optical fiber 113.

The light intensity sensor 114 converts the light into an electrical signal. The electrical signal is processed by the control unit 118 into an image as a fundus image and the fundus image is displayed on a display 119.

The wavefront sensor 115 is connected to a compensation optical controller 116. The received wavefront is transferred to the compensation optical controller 116.

The wavefront compensation device 108 is also connected to the compensation optical controller 116 and performs modulation instructed from the compensation optical controller 116.

The compensation optical controller 116 calculates a modulation amount for compensation to obtain wavefront having no aberration based on the wavefront obtained by the wavefront sensor 115, and instructs the wavefront compensation device 108 to perform the compensation according to the modulation amount.

The wavefront measurement and the instruction to the wavefront compensation device are repeated and feedback control is performed to always obtain a suitable wave front.

For aberration compensation, it is necessary to divide a part of signal light by the light division portion 106 to measure the wavefront.

A feature of this embodiment is as follows. The effectiveness of compensation, that is, whether or not an effect obtained by continuous compensation using the adaptive optics (AO) exceeds, even during image sensing, the influence of the reduction in image sensing light amount, which is caused by the division is determined, and the division, is made when the effect exceeds the influence.

In this embodiment, the beam splitter having a division ratio of 80 (transmission):20 (reflection) is used as the light division portion 106. Therefore, when light is divided in order to measure the wavefront by the wavefront sensor 115, the fundus image sensing light amount is reduced by 20%.

When an image quality improvement effect obtained by aberration compensation exceeds the influence of the light amount reduced by 20%, the compensation is performed even while the image of the fundus is sensed.

The light division portion 106 is inserted into the optical path of the measuring light 105 to perform optical path division.

Next, a procedure of a control method for an optical image sensing apparatus according to this embodiment is described with reference to a flow chart illustrated in FIG. 3.

First, in Step S101, control processing starts.

Next, in Step S102, a resolution is set.

To be specific, the control unit 118 controls the resolution setting unit 117 through the resolution controller 120 and adjusts the beam diameter of the measuring light to set the resolution.

Next, in Step S103, for aberration compensation, the light division portion 106 is inserted into the optical path of the measuring light 105 under the control of the control unit 118 to divide light to the wavefront sensor. In next Step S104 and subsequent steps, processing using the compensation optical system is performed.

In the fundamental flow for the compensation optical system, while the light is divided to the wavefront sensor 115 by the light division portion 106 (also referred to as division unit), an aberration is measured by the wavefront sensor 115 in Step S104.

Next, in Step S106, a compensation amount is calculated by the compensation optical controller 116 based on a result obtained by the measurement.

Next, in Step S107, the wavefront compensation device 108 is driven under the control of the compensation optical controller 116. The above-mentioned flow is repeated as the processing using the compensation optical system.

During this flow, after the aberration is measured in Step S104, whether or not the aberration amount is smaller than a preset reference value is determined by the compensation optical controller 116 in Step S105.

The reference value may be a value specific to the apparatus or may be set by a photographer.

When the aberration amount exceeds the reference value, Step S106 and subsequent processings are executed.

On the other hand, when the aberration amount is smaller than the reference value, the processing proceeds to Step S108.

In Step S108, whether or not the image quality is to be improved by the continuous aberration compensation even when the light amount loss is 20% as described above is determined.

In this embodiment, two parameters of resolution and image sensing signal intensity are used to determine whether or not the image quality is to be improved.

The aberration compensation causes the increase in resolution. The image quality improves with the improvement of light receiving efficiency. In contrast to this, a light receiving amount is reduced by 20% because of the division. The image quality reduces with the reduction in light receiving amount.

Therefore, whether or not the image quality is to be finally improved is determined based on both the parameters.

The determination is made by the control unit 118 for controlling the SLO in this embodiment. The control unit 118 may include a computer system.

Examples of the determination are described with reference to FIGS. 4A to 4D.

Figure 4A:
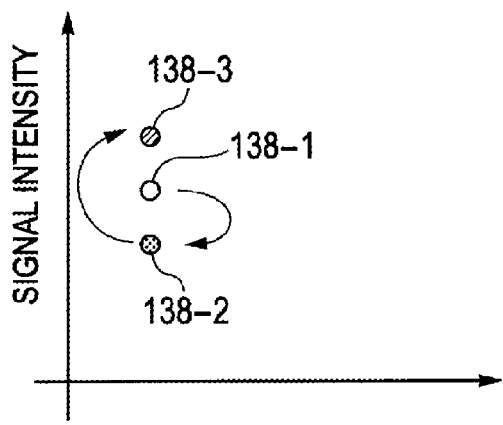
FIGS. 4A, 4B, 4C and 4D illustrate examples of effects on image quality in the present invention.
Figure 4B:
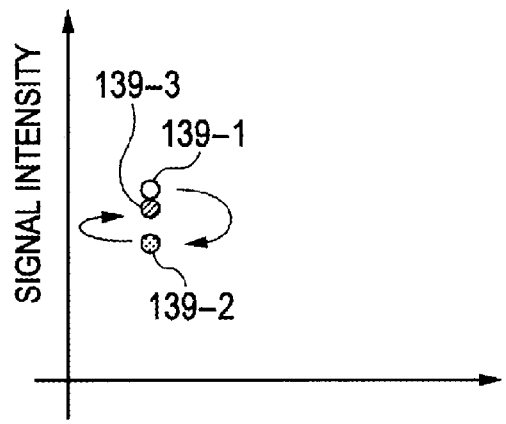

FIGS. 4A and 4B illustrate examples in which whether or not the image quality is to be improved is determined based on only the signal intensity.

FIG. 4A illustrates an initial signal intensity 138-1 in the case where aberration compensation is not performed. When the measuring light is divided for aberration measurement, the light receiving amount is reduced by 20% and the signal intensity is reduced from the initial signal intensity 138-1 to a signal intensity 138-2.

Note that, when the aberration compensation is performed, the light receiving efficiency is improved to increase the signal intensity, and hence the signal intensity is increased to a signal intensity 138-3.

That is, the signal intensity 138-3 in the case where the compensation is performed exceeds the signal intensity 138-1 in the case where the compensation is not performed, and hence it is determined that the image quality is to be improved by the continuous compensation.

In contrast to this, FIG. 4B illustrates the case where the signal intensity is not expected to be increased by the compensation. As in the case illustrated in FIG. 4A, beam division is performed for compensation, and hence the light receiving intensity is reduced from an initial signal intensity 139-1 to a signal intensity 139-2.

The signal intensity is increased by the compensation, but an effect obtained by the compensation is small and the signal intensity is only increased to a signal intensity 139-3. In this case, the signal intensity 139-3 is lower than the initial signal intensity 139-1 and thus the image quality is reduced, and hence there is no merit in continuing the compensation. Therefore, it is determined not to perform the compensation.

Next, examples in which whether or not the image quality is to be improved is determined based on the signal intensity and the resolution are described with reference to FIGS. 4C and 4D.

Figure 4C:
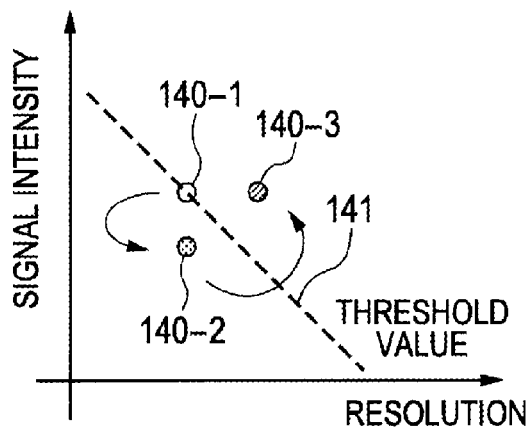

FIG. 4C illustrates an initial signal intensity-resolution point 140-1 in the case where the compensation is not performed. Even when the measuring light is divided for aberration measurement, the resolution is not reduced and only the light receiving amount is reduced, and hence the signal intensity-resolution point is shifted to a signal intensity-resolution point 140-2.

When the compensation is performed, the light receiving efficiency is improved to increase the signal intensity and the resolution is improved, and hence the signal intensity-resolution point is shifted to a signal intensity-resolution point 140-3.

Whether or not the image quality is to be improved is determined based on the combination of the signal intensity and the resolution. Therefore, a threshold value (indicated by broken line) 141 as illustrated in FIGS. 4C and 4D is set as a reference to determine whether or not the image quality is to be improved.

When the signal intensity-resolution point 140-3 is compared with the initial signal intensity-resolution point 140-1, the signal intensity is not significantly increased but the resolution is improved, and hence the signal intensity-resolution point 140-3 exceeds the threshold value as the reference for determination.

Therefore, it is determined that there is a compensation effect.

Figure 4D:
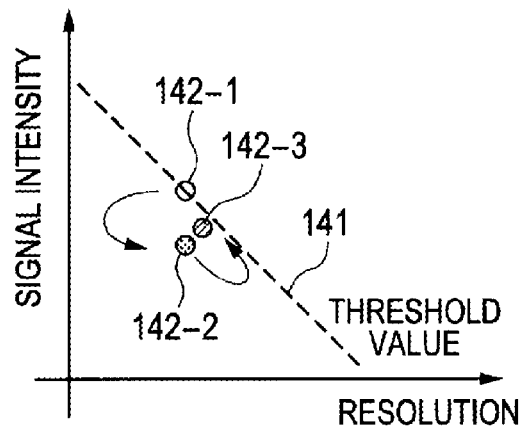

On the other hand, in FIG. 4D, the signal intensity is reduced by beam division to shift an initial signal intensity-resolution point 142-1 to a signal intensity-resolution point 142-2. When the compensation is performed, the signal intensity-resolution point 142-2 is shifted to the signal intensity-resolution point 142-3 to improve the signal intensity and the resolution.

However, the signal intensity-resolution point 142-3 does not reach to the threshold value as the reference for determination, and hence it is determined that there is no compensation effect.

Whether or not the signal intensity and the resolution are to be improved by the compensation may be determined based on, for example, the beam diameter for sensing the image of the fundus, the change in light amount which is caused by the compensation, aberration data of the measured eye, the performance of the compensation device, an image sensing time, and a temporal change in aberration.

An image quality threshold value for a combination of the signal intensity and the resolution may be determined based on the signal intensity and the resolution which are weighted. A weighting ratio is changed depending on an image to be obtained. For example, a mode which is suitable for high-magnification image sensing and used to improve the resolution having priority over the signal intensity and a mode which is suitable for wide-angle image sensing and used to improve the signal intensity having priority over the resolution may be set and selected by an operator.

In FIGS. 4C and 4D, the threshold value is set to include the initial value of the image quality. The threshold value may be set to obtain higher image quality than that of the initial value depending on the degree of desired image quality.

When it is determined in Step S108 that the compensation effect exceeds the light amount loss caused by beam division, the processing proceeds to Step S117. When it is determined that the compensation effect does not exceed the light amount loss, the processing proceeds to Step S109 and beam division to the wavefront sensor 115 is canceled (division unit is retreated).

Next, a shape of the compensation device 108 in the case where the beam division to the wavefront sensor 115 is canceled is described.

When the beam division is canceled in Step S109, the shape of the compensation device 108 is held to a shape immediately before canceling.

Therefore, division loss may be suppressed while the aberration compensation effect is maintained to some extent.

The compensation device 108 may be set in an initial device state. In this case, the wavefront compensation is not affected by the aberration compensation.

In Step S110, image sensing is performed. In Step S111, whether or not an image sensing completion request is received is confirmed. When the image sensing completion request is not received, processing returns to Step S110 and the image sensing is performed again. When the image sensing completion request is received, the processing proceeds to Step S112 and the control processing is ended.

When the processing proceeds to Step S117, image sensing is performed in Step S117. In Step S118, whether or not the image sensing is completed is confirmed.

When the image sensing completion request is not received, the processing of Steps S113 to S116 using the compensation optical system is performed, and then the image sensing is performed again in Step S117.

In this embodiment, the image sensing and the aberration compensation processing are sequentially performed, but may be performed in parallel.

When the image sensing completion request is confirmed in Step S118, the beam division is canceled in Step S119 and the control processing is ended in Step S112.

As described above, according to this embodiment, the operation of the compensation optical system may be suitably controlled depending on image sensing conditions.

Suitable aberration compensation corresponding to image sensing conditions may be executed, and hence high-quality fundus image sensing may be achieved and image quality may be prevented from being reduced by aberration compensation.

When it is determined that there is no aberration compensation effect, the division of aberration measurement light which becomes waste light may be canceled.

Second Embodiment

A second embodiment describes a different structural example, from the first embodiment, in which the present invention is applied to an SLO.

An optical image sensing apparatus according to this embodiment has the same structure as in the first embodiment illustrated in the schematic diagram of FIG. 1.

Next, a procedure of a control method for the optical image sensing apparatus according to this embodiment is described with reference to a flow chart illustrated in FIG. 5.

This embodiment has a feature in that a threshold value of a beam diameter for which dynamic aberration compensation is required is set in advance, and whether or not beam division for aberration measurement is performed is determined based on a measured beam diameter.

First, in Step S101, control processing starts.

Next, in Step S102, a resolution is set.

Next, in Step S103, for aberration compensation, the light division portion 106 is inserted into the optical path of the measuring light 105 to divide the light to the wavefront sensor 115.

In next Step S104 and subsequent steps, processing using the compensation optical system is performed.

The fundamental flow for the compensation optical system is the same as in the first embodiment, and Steps S104 to S107 are repeated while the light is divided to the wavefront sensor 115 by the light division portion 106.

During this flow, after the aberration is measured in Step S104, whether or not the aberration amount is smaller than a preset reference value is determined by the compensation optical controller 116 in Step S105.

When the aberration amount exceeds the reference value, Step S106 and subsequent processings are executed.

On the other hand, when the aberration amount is smaller than the reference value, the processing proceeds to Step S120.

In Step S120, whether or not a measured beam diameter exceeds the threshold value of the beam diameter for which dynamic aberration compensation is required is determined.

When the measured beam diameter is large, the influence of aberration on image quality is large, and hence the aberration compensation effect is large.

In contrast to this, when the measured beam diameter is small, the image quality is not significantly improved even by aberration compensation, and hence a light receiving amount loss caused by beam division becomes larger.

Therefore, whether or not the dynamic aberration compensation is required may be determined based on the measured beam diameter.

The threshold value of the beam diameter for which the dynamic aberration compensation is required may be calculated based on general aberration information of the eye and compensation performance of the apparatus, or may be calculated based on measured aberration information of the eye to be measured in addition to the general aberration information and the compensation performance.

When the measured beam diameter exceeds the threshold value, the processing proceeds to Step S117. When the measured beam diameter does not exceed the threshold value, the processing proceeds to Step S109.

In Step S109, beam division to the wavefront sensor 115 is canceled. In Step S110, image sensing is performed.

In Step S111, whether or not the image sensing completion request is received is determined. When the image sensing completion request is not received, processing returns to Step S110 and the image sensing is performed again. When the image sensing completion request is received, the processing proceeds to Step S112 and the control processing is ended.

When the processing proceeds to Step S117, image sensing is performed. In Step S118, whether or not the image sensing is completed is determined.

When the image sensing completion request is not received, the processing of Steps S113 to S116 using the compensation optical system is performed, and then the image sensing is performed again in Step S117.

In this embodiment, the image sensing and the aberration compensation processing are sequentially performed, but may be performed in parallel.

When the image sensing completion request is confirmed in Step S118, the beam division is canceled in Step S119 and the control processing is ended in Step S112.

As described above, according to this embodiment, the operation of the compensation optical system may be suitably controlled depending on image sensing conditions.

Aberration compensation suited to image sensing conditions may be executed, and hence high-quality fundus image sensing may be achieved and image quality may be prevented from being reduced by aberration compensation. In particular, the effectiveness of aberration compensation is determined based on the predetermined value, and hence a calculation load may be reduced.

Third Embodiment

Figure 6:
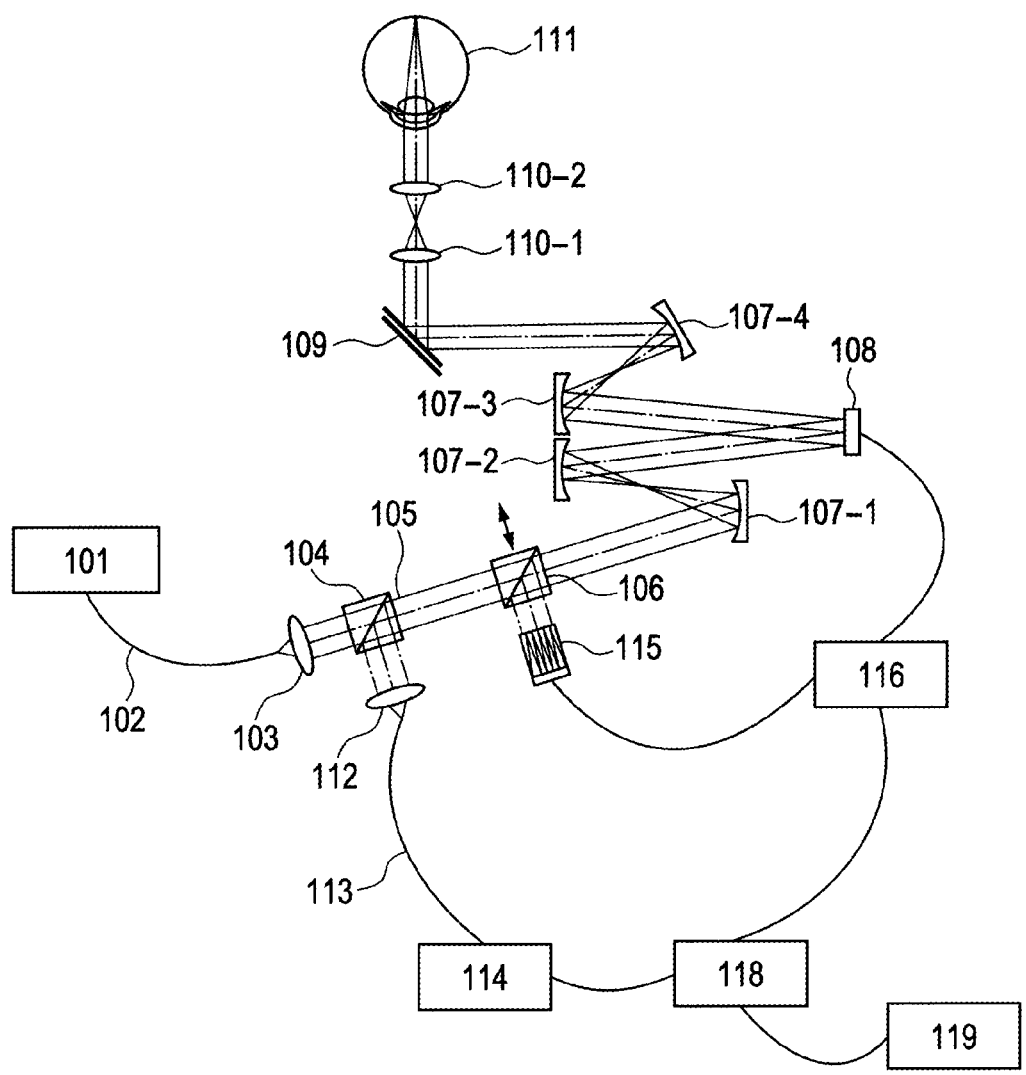
FIG. 6 is a schematic diagram illustrating a structural example of the SLO in a third embodiment of the present invention.

A third embodiment describes a different structural example, from the first and second embodiments, in which the present invention is applied to a SLO, with reference to FIG. 6.

An optical image sensing apparatus according to this embodiment has fundamentally the same structure as in the first embodiment illustrated in the schematic diagram of FIG. 1, but does not include the resolution setting unit 117. Therefore, measurement is performed at a specific resolution.

Figure 7:
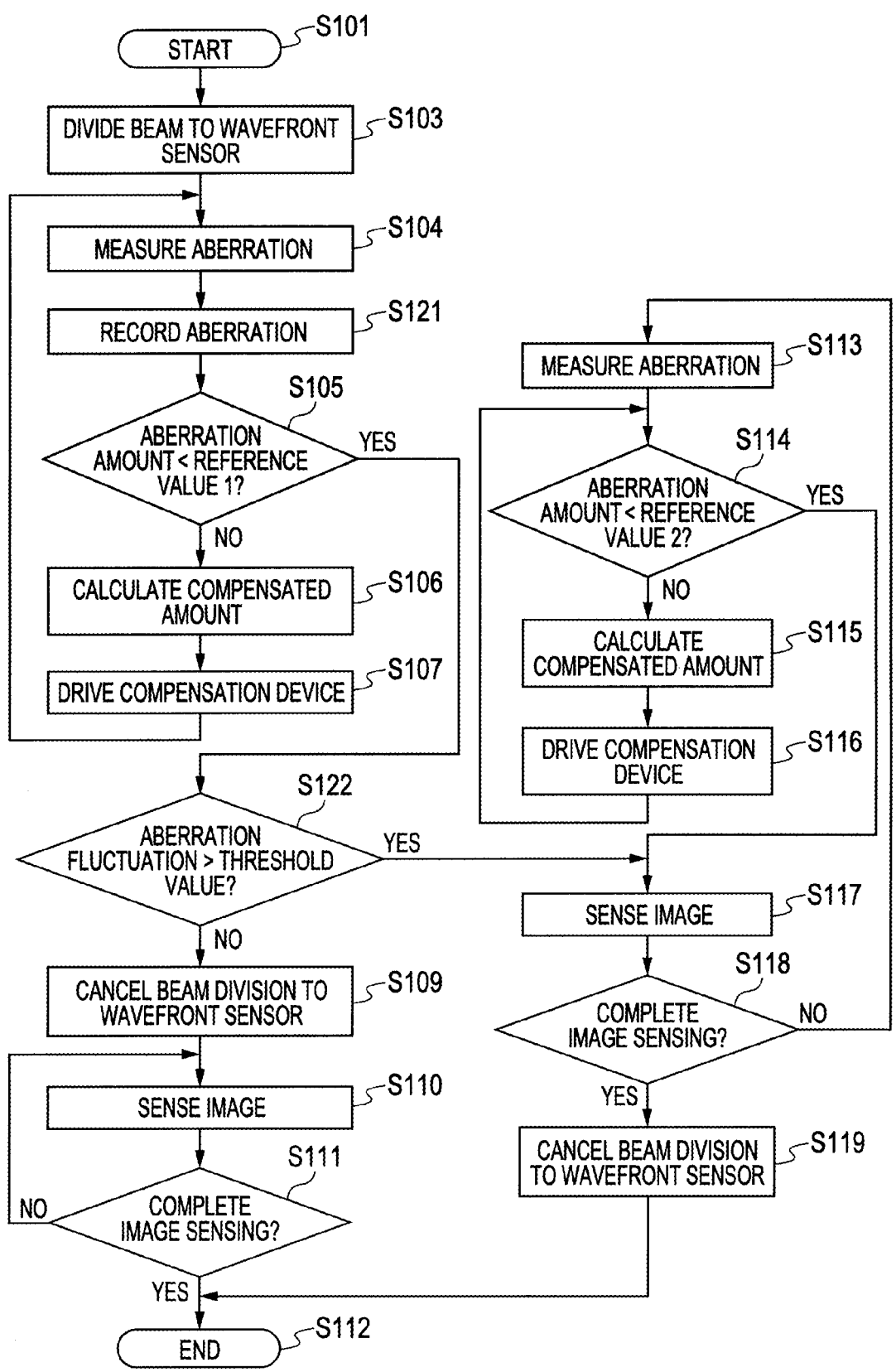
FIG. 7 is a flow chart illustrating a procedure of a control method for an optical image sensing apparatus according to the third embodiment of the present invention.

Next, a procedure of a control method for the optical image sensing apparatus according to this embodiment is described with reference to a flow chart illustrated in FIG. 7.

This embodiment has a feature in that an image quality improvement effect by dynamic compensation is determined based on a temporal fluctuation in aberration measured during aberration compensation.

First, in Step S101, control processing starts.

Next, in Step S103, for aberration compensation, the light division portion 106 is inserted into the optical path of the measuring light 105 to divide the light to the wavefront sensor 115.

In next Step S104 and subsequent steps, processing using the compensation optical system is performed.

The fundamental flow for the compensation optical system is the same as in the first embodiment. Steps S104, S121, S105, S106, and S107 are repeated while the light is divided to the wavefront sensor 115 by the light division portion 106.

After an aberration is measured in Step S104, the measured aberration data is recorded in a recording apparatus (not shown) in Step S121.

In Step S105, whether or not the measured aberration amount is smaller than a preset reference value is determined by the compensation optical controller 116. When the aberration amount exceeds the reference value, Step S106 and the subsequent processing are executed.

On the other hand, when the aberration amount is smaller than the reference value, the processing proceeds to Step S122.

In Step S122, a temporal fluctuation in aberration is calculated based on the aberration data recorded in Step S121, and whether or not the temporal fluctuation exceeds a threshold value is determined.

When the temporal fluctuation is large, an aberration is likely to greatly fluctuate during fundus image sensing, to thereby significantly reduce image quality, and hence dynamic aberration compensation is necessary.

In contrast to this, when an aberration fluctuation amount is small and thus aberration does not greatly fluctuate, the aberration is expected not to greatly fluctuate even during fundus image sensing, and hence the dynamic aberration compensation is determined to be unnecessary.

When the fluctuation in aberration exceeds the threshold value, the processing proceeds to Step S117. When it is determined that the fluctuation in aberration does not exceed the threshold value, the processing proceeds to Step S109.

In Step S109, division control is performed so that the light division portion located on an optical path of the return beam is retreated (removed) from the optical path to cancel the beam division to the wavefront sensor 115. In Step S110, image sensing is performed.

In Step S111, whether or not an image sensing completion request is received is determined. When the image sensing completion request is not received, processing returns to Step S110 and the image sensing is performed again. When the image sensing completion request is received, the processing proceeds to Step S112 and the control processing is ended.

When the processing proceeds to Step S117, image sensing is performed. In Step S118, whether or not the image sensing is completed is determined.

When the image sensing completion request is not received, the processing of Steps S113 to S116 using the compensation optical system is performed, and then the image sensing is performed again in Step S117.

In this embodiment, the image sensing and the aberration compensation processing are sequentially performed, but may be performed in parallel.

When the image sensing completion request is confirmed in Step S118, the beam division is canceled in Step S119 and the control processing is ended in Step S112.

As described above, according to this embodiment, the operation of the compensation optical system may be suitably controlled depending on image sensing conditions.

Aberration compensation suited to image sensing conditions may be executed, and hence high-quality fundus image sensing may be achieved and image quality may be prevented from being reduced by aberration compensation.

In particular, the influence on actual image quality is considered, and hence the effectiveness may be more accurately determined.

Fourth Embodiment

A fourth embodiment describes a structural example in which the present invention is applied to an optical coherent tomography (OCT) apparatus provided with a compensation optical function.

Figure 8:
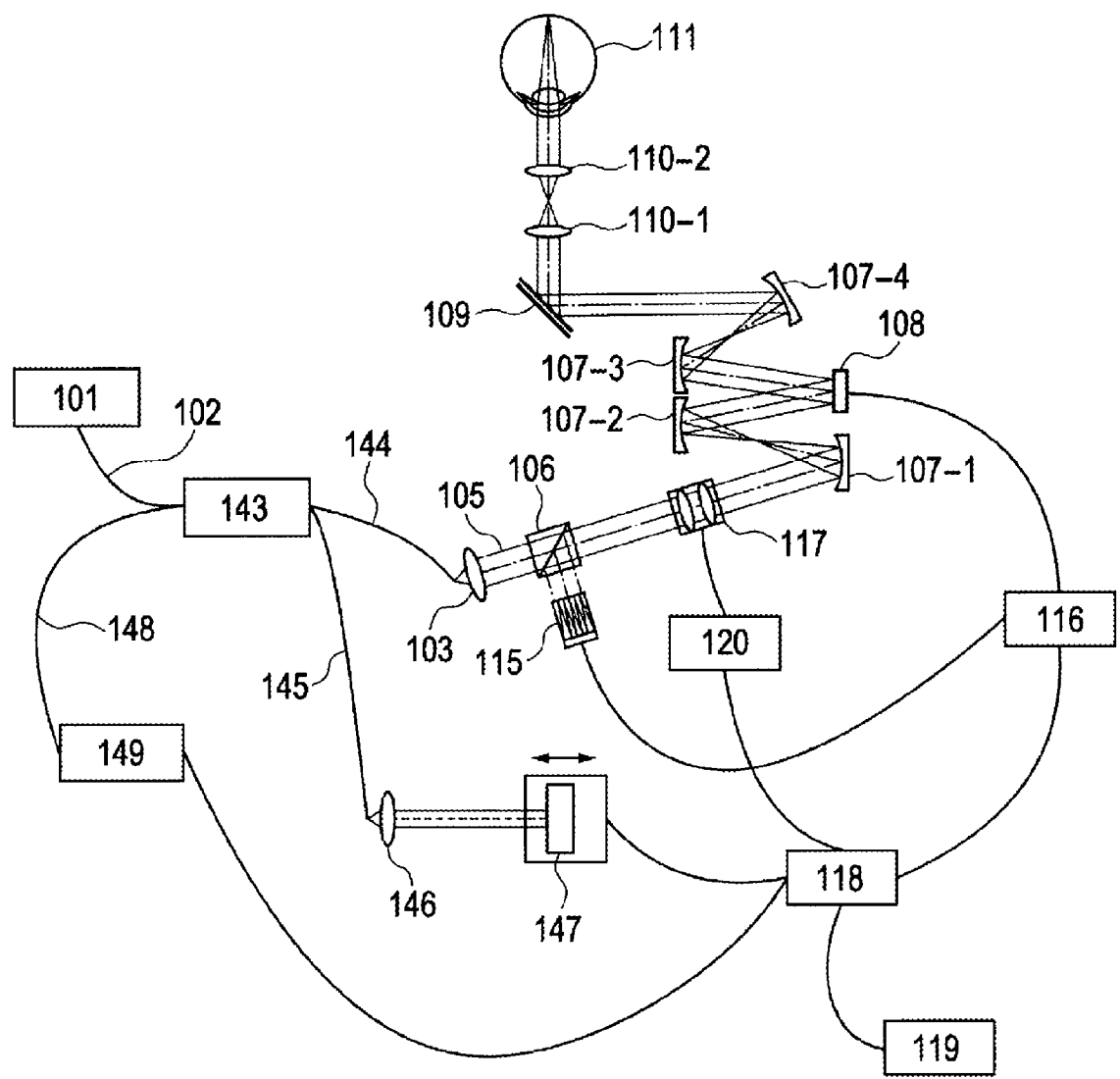
FIG. 8 is a schematic diagram illustrating a structural example of an optical coherent tomography (OCT) apparatus in a fourth embodiment of the present invention.

FIG. 8 is a schematic diagram illustrating a structural example of the OCT.

In FIG. 8, the light source 101 used in this embodiment is an SLD light source having a wavelength of 840 nm.

The light source 101 desirably has low coherence. An SLD having a wavelength width equal to or longer than 30 nm is suitably used. An ultra-short pulse laser, for example, a titanium sapphire laser may be used as the light source.

Light projected from the light source 101 is guided to a fiber coupler 143 through the single-mode optical fiber 102.

An optical path is divided by the fiber coupler 143 into a signal light path 144 and a reference light path 145. The fiber coupler to be used has a division ratio of 10:90 and is provided so that 10% of the projected light travels on the signal light path 144.

The light traveling on the signal light path 144 is converted into collimated light by the collimator 103.

The collimator 103 and the subsequent elements are the same as in the first embodiment. The light is projected to the eye 111 through the compensation optical system and the scanning optical system.

Reflected scattering light from the eye 111 travels along the same path again and is guided through the optical fiber (signal light path) 144 to reach the fiber coupler 143.

In this embodiment, the resolution setting unit 117 is provided closer to the eye with respect to the light division portion 106. Therefore, even when a resolution is adjusted, a beam diameter of light entering the wavefront sensor 115 is not changed.

In contrast to this, reference light traveling on the reference light path 145 exits from a collimator 146 to be reflected on an optical path length varying portion 147, and returns to the fiber coupler 143 again.

The signal light and the reference light which reach the fiber coupler 143 are superimposed on each other and guided to a spectroscope 149 through an optical fiber 148.

A tomographic image of the fundus is formed by the control unit 118 based on interference light information obtained by the spectroscope 149.

The control unit 118 may control the optical path length varying portion 147 to obtain an image at a desired depth position.

As in the first embodiment, a wavefront is measured by the wavefront sensor 115 and the wavefront compensation device 108 is driven to cancel an aberration of the wave front.

Even in this embodiment, processing is performed through the steps illustrated in FIG. 3 as in the first embodiment. When it is determined that the image quality is to be improved by the aberration compensation, the image sensing of the fundus is performed during the dynamic aberration compensation.

The tomographic image is obtained by the OCT. However, when an NA of incident light is increased to improve the resolution, a depth of field becomes shallower, and hence the tomographic image includes a focused region and a non-focused region.

Therefore, it is conceivable to employ a method of dividing an image sensing region in a depth direction by a width corresponding to the depth of field to perform image sensing and then combining images at respective depths to obtain a tomographic image focused on the entire region.

In this case, a region in the depth direction which is obtained by each image sensing is adjusted according to the resolution changed in Step S102 illustrated in FIG. 3, and hence an image having a large focused region may be easily sensed at high speed.

As described above, according to this embodiment, the operation of the compensation optical system may be suitably controlled based on the image sensing conditions.

A suitable aberration compensation method may be executed even for the tomographic image of the fundus, and hence the high-quality tomographic image of the fundus may be obtained and the reduction in image quality may be prevented.

With respect to the control method for the optical image sensing apparatus according to each of the embodiments as described above, programs for causing a computer to execute the control method may be produced and stored in a storage medium to be read by the computer.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-019120, filed Jan. 29, 2010, which is hereby incorporated by reference herein in its entirety.

The invention claimed is:

1. A compensation optical apparatus, comprising:
    a division unit for dividing a return beam from a measured object;
    an aberration measurement unit for measuring an aberration caused by the measured object, with a divided beam from the division unit;
    an aberration compensation unit for performing aberration compensation based on the aberration measured by the aberration measurement unit;
    a projection unit for projecting a beam obtained by the aberration compensation in the aberration compensation unit to the measured object;
    an acquirement unit for acquiring a value exhibiting a state of the measured object based on the return beam from the measured object, which is obtained by the beam projected from the projection unit; and
    a control unit for retreating the division unit from an optical path based on the value acquired by the acquirement unit.

2. A compensation optical apparatus according to claim 1, wherein:
    the value exhibiting the state of the measured object comprises an amount of the aberration measured by the aberration measurement unit; and
    the control unit retreats the division unit from the optical path when the amount of the aberration is equal to or larger than a predetermined aberration amount.

3. A compensation optical apparatus according to claim 1, further comprising a varying unit for varying a beam diameter of the beam obtained by the aberration compensation in the aberration compensation unit, wherein:

the value exhibiting the state of the measured object comprises the beam diameter of the beam obtained by the aberration compensation in the aberration compensation unit; and the control unit retreats the division unit from the optical path when the beam diameter varied by the varying unit is smaller than a predetermined diameter.

4. A compensation optical apparatus according to claim 3, wherein the varying unit reduces the beam diameter of the beam obtained by the aberration compensation in the aberration compensation unit when an amount of the aberration measured by the aberration measurement unit is equal to or larger than a predetermined aberration amount.

5. A compensation optical apparatus according to claim 1, wherein:

the value exhibiting the state of the measured object comprises a fluctuation amount of the aberration measured by the aberration measurement unit; and the control unit retreats the division unit from the optical path when the fluctuation amount is smaller than a predetermined fluctuation amount.

6. An image sensing apparatus for sensing an image of a measured object, comprising:

the compensation optical apparatus according to claim 1; and an image acquirement unit for acquiring the image of the measured object based on the return beam from the measured object under a state in which a compensation characteristic obtained by the aberration compensation unit is maintained and the division unit is retreated from the optical path.

7. An image sensing apparatus for sensing an image of a measured object, comprising:

the compensation optical apparatus according to claim 1; and an image acquirement unit for acquiring the image of the measured object based on a part of the return beam from the measured object under a state in which the division unit is inserted into the optical path during the aberration compensation performed by the aberration compensation unit.

8. An image sensing apparatus for sensing an image of a measured object, comprising:

the compensation optical apparatus according to claim 1; and an image acquirement unit for acquiring the image of the measured object based on the return beam from the measured object, wherein:

the value exhibiting the state of the measured object comprises a value exhibiting quality of the image; and the control unit retreats the division unit from the optical path when the value exhibiting the quality of the image is smaller than a predetermined value.

9. An image sensing apparatus according to claim 8, wherein the control unit retreats the division unit from the optical path when a value exhibiting quality of an image obtained under a state in which the division unit is retreated from the optical path is larger than a value exhibiting quality of an image obtained under a state in which the division unit is inserted into the optical path.

10. An image sensing apparatus according to claim 8, wherein the value exhibiting the quality of the image comprises at least one of a resolution and an intensity.

11. A compensation optical apparatus, comprising:

an aberration measurement unit for measuring an aberration caused by a measured object based on a return beam from the measured object;

an aberration compensation unit for compensating an aberration in accordance with the aberration measured by the aberration measurement unit;

a projection unit for projecting onto the measured object a beam compensated by the aberration compensation unit; and a division unit capable of being inserted into and retreated from an optical path of the beam projected from the projection unit, for dividing the return beam from the measured object caused from the projected beam, and guiding a part of the return beam into the aberration measurement unit.

12. A compensation optical apparatus according to claim 11, further comprising a control unit for retreating the division unit from the optical path in accordance with an aberration amount measured by the aberration measurement unit.

13. A compensation optical apparatus according to claim 12, wherein the control unit retreats the division unit from the optical path in a case that the aberration amount is equal to or less than a predetermined value.

14. An image sensing apparatus for sensing an image of the measured object, comprising:

the compensation optical apparatus according to claim 12; and an image acquirement unit for acquiring the image of the measured object based on the return beam from the measured object in accordance with the retreating the division unit.

15. An image sensing apparatus for sensing an image of the measured object, comprising:

the compensation optical apparatus according to claim 12; and an image acquirement unit for acquiring the image of the measured object based on the return beam from the measured object under a state in which a compensation characteristic obtained by the aberration compensation unit is maintained and the division unit is retreated from the optical path.

* * * * *